United States Patent [19]  
Bigg et al.

[11] Patent Number: 4,659,731  
[45] Date of Patent: Apr. 21, 1987

[54] 2-(4,5-DIHYDRO-1H-IMIDAZOL-2-YL)-2,3-DIHYDROINDOLE DERIVATIVES AND THEIR APPLICATION AS $\alpha_2$ RECEPTOR ANTAGONIST OR $\alpha_1$ RECEPTOR AGONISTS

[75] Inventors: Denis Bigg, Jouy en Josas; Jacques Menin, Vitry S/Seine; Christian Maloizel, Meudon; Jean Merly, Fontenay Aux Roses, all of France

[73] Assignee: Synthelabo, Paris, France

[21] Appl. No.: 826,500

[22] Filed: Feb. 5, 1986

[30] Foreign Application Priority Data

Feb. 8, 1985 [FR] France ................ 85 01774  
Feb. 8, 1985 [FR] France ................ 85 01775

[51] Int. Cl.$^4$ ............... A61K 31/415; C07D 403/00  
[52] U.S. Cl. .................................. 514/397; 548/348  
[58] Field of Search .................... 548/348; 514/397

[56] References Cited  
U.S. PATENT DOCUMENTS  
3,586,695 6/1971 Wysong et al. ................ 548/348

Primary Examiner—Henry R. Jiles  
Assistant Examiner—Robert C. Whittenbaugh  
Attorney, Agent, or Firm—Wegner & Bretschneider

[57] ABSTRACT

Derivatives of formula (I)

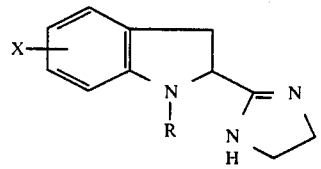

in which X denotes a hydrogen or halogen atom, an alkoxy radical, an alkyl radical or an allyloxy radical, and R denotes a linear or branched alkyl radical, a cycloalkylalkyl radical, an alkenyl radical, an arylalkyl radical which can bear one or more substituents chosen from halogen atoms and methyl, methoxy and methylenedioxy radicals, or alternatively an optionally substituted phenyl radical, as well as the addition salts thereof with pharmaceutically acceptable acids produce an $\alpha_2$-receptor antagonist effect.

15 Claims, No Drawings

2-(4,5-DIHYDRO-1H-IMIDAZOL-2-YL)-2,3-DIHYDROINDOLE DERIVATIVES AND THEIR APPLICATION AS $\alpha_2$ RECEPTOR ANTAGONIST OR $\alpha_1$ RECEPTOR AGONISTS The present invention relates to 2-(4,5-dihydro-1H-imidazol-2-yl)-2,3-dihydroindole derivatives, the preparation thereof and their application in therapy.

The compounds of the invention correspond to the general formula (I)

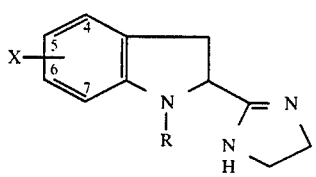
(I)

in which

X is at position 4, 5, 6 or 7 and denotes a halogen atom, a $(C_{1-4})$alkoxy radical, a $(C_{1-4})$alkyl radical or an allyloxy radical, or alternatively, when R denotes a phenyl radical, optionally substituted, X can also denote a hydrogen atom and R denotes a linear or branched $(C_{1-6})$alkyl radical, a $(C_{3-6})$cycloalkyl-$(C_{1-4})$alkyl radical, a $(C_{3-6})$alkenyl radical, an aryl-$(C_{1-4})$alkyl radical which can bear one or more substituents chosen from halogen atoms and methyl, methoxy and methylenedioxy radicals, or alternatively an optionally substituted phenyl radical of formula

in which Y denotes a hydrogen or halogen atom or a linear or branched $(C_{1-6})$alkyl radical or a linear or branched $(C_{1-6})$alkoxy radical.

The compounds of the invention can exist in the form of racemates or enantiomers which form part of the invention. The pharmaceutically acceptable salts of the compounds (I) also form part of the invention.

A first series of preferred compounds is that in the formula (I) of which X is a chlorine or fluorine atom or a methyl, methoxy or allyloxy radical (more especially at position 4, 6 or 7), and R is an alkyl, benzyl, allyl or cyclopropylmethyl radical.

Another series of preferred compounds is that in the formula (I) of which X is a hydrogen atom or a methyl radical (more especially at position 4) and R is a phenyl radical which is either unsubstituted or bears a methyl, ethyl, propyl, methoxy, ethoxy or propoxy radical (more especially at position 3 or 4).

Compounds of the invention in the formula (I) in which R denotes an alkyl, cycloalkylalkyl, alkenyl or aralkyl radical can be prepared by reacting a compound of formula (IV)

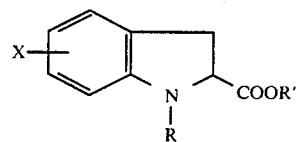
(IV)

wherein R' is $(C_{1-4})$alkyl and R and X are as defined in relation to formula (I) except that R is other than a group

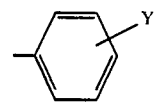

with ethylene diamine in the presence of trimethyl aluminium.

Suitably the compounds of formula (IV) are produced by reacting a compound of formula (III)

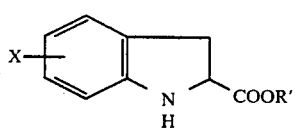
(III)

wherein R' is $(C_{1-4})$alkyl and X is as defined in relation to compounds of formula (I) with a compound RZ wherein R is as defined in relation to compounds of formula (I) except that R is other than a group

and Z is a labile group. Preferably Z is an iodine or bromine atom and the reaction is conducted in a solvent such as acetone, methyl ethyl ketone or dimethylformamide, at room temperature or at a higher temperature, in the presence of a base such as potassium carbonate. Conveniently the reaction may be catalysed, for example by adding sodium iodide.

Suitably the compounds of formula (III) are produced by hydrogenation of the known compounds of formula (II)

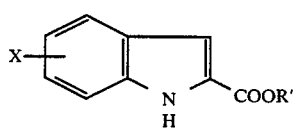
(II)

wherein R' is $(C_{1-4})$alkyl and X is as defined in relation to compounds of formula (I), preferably using gaseous hydrogen chloride and tin.

The compounds of formula (I) in which R is a phenyl radical bearing a substituent Y are produced by reacting a compound of formula (VIII)

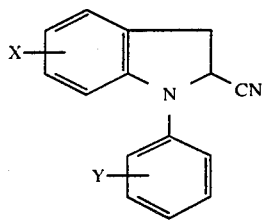

(VIII)

wherein X and Y are as defined in relation to compounds of formula (I) with the diethylamine in the presence of trimethylaluminium.

The compounds of formula (VIII) are suitably obtained by reacting a compound of formula (VII)

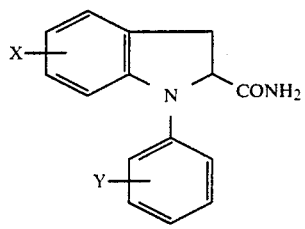

(VII)

wherein X and Y are as defined in relation to compounds of formula (I) with a sulphonyl chloride in the presence of a tertiary amine such as pyridine or by any other known method. Preferably p-toluenesulphonyl chloride is used.

The compounds of formula (VII) are suitably obtained by reducing a compound of formula (VI)

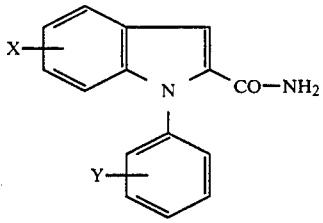

(VI)

wherein X and Y are as defined in relation to compounds of formula (I) preferably using liquid ammonia and sodium.

The compounds of formula (VI) are suitably obtained by reacting a known compound of formula (V)

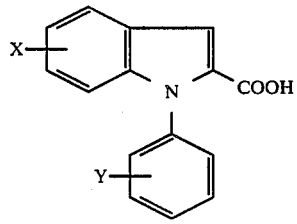

(V)

wherein X and Y are as defined in relation to compounds of formula (I) with ammonia in the presence of carbonyl diimidazole. Compounds of formula (I) wherein X is hydrogen may also be produced by reacting a compound of formula (VIII')

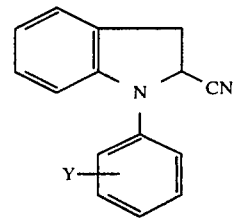

(VIII')

wherein Y is as defined in relation to compounds of formula (I) with ethylenediamine in the presence of hydrogen sulphide. Compounds of formula (VIII') are obtained by the method described above from compounds of formula (VII) wherein X is hydrogen, which may, in turn, be obtained from compounds of formula (VI) wherein X is hydrogen, as described above.

Compounds of formula (VI) wherein X is hydrogen may be obtained by the method described above or by reacting a compound of formula (V')

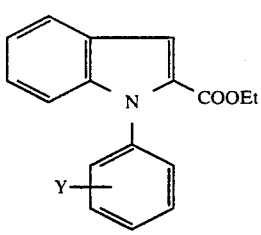

(V')

wherein Y is as defined in relation to compounds of formula (I) with ammonium chloride and trimethylaluminium at elevated temperature and hydrolysing the product, for instance using hydrochloric acid.

The compounds of the invention are powerful $\alpha_2$-antagonists which can be used for the treatment of depression (either alone or in combination with a product which inhibits neuronal uptake mechanisms), the treatment of hypotension, the treatment of postoperative paralytic ileum, the treatment of asthma and obesity, the treatment of diabetes and the treatment of impotence.

Furthermore, some of the compounds of the invention are also $\alpha_1$-agonists, which possess value as nasal vasoconstrictors.

The pharmaceutical compositions having $\alpha_2$-antagonistic activity can be in a form suitable for oral, rectal or parenteral administration; for example, in the form of capsules, tablets, granules, gelatin capsules or liquid solutions, syrups or suspensions for oral administration, and can contain the appropriate excipients.

The pharmaceutical compositions having $\alpha_1$-agonistic activity, which can be used for the treatment of nasal congestion, can be in a form suitable for external or local administration, for example in the form of aerosols or solutions for spraying, and can contain the appropriate excipients.

The daily dosage can range from 0.1 to 10 mg/kg p.o.

The examples which follow illustrate the invention. The IR and NMR spectra and the analyses confirm the structure of the compounds.

EXAMPLE 1

2-(4,5-Dihydro-1H-imidazol-2-yl)-1-benzyl-4-chloro-2,3-dihydro-1H-indole and its fumarate.

1.1. Ethyl 4-chloro-2,3-dihydro-1H-indole-2-carboxylate.

In a 2-l three-necked flask which is maintained at −50° C. in a mixture of dry ice and isopropanol, 350 ml of ethanol are introduced and a stream of hydrogen chlorise gas is passed in.

33,0 g (0.148 mole) of ethyl 4-chloro-1H-indole-2-carboxylate are then introduced and 105.4 (0.888 g-at) of tin are then added in a single portion. The reaction mixture is stirred and allowed to return slowly to room temperature. The solution is stirred for 40 h and treated with a stream of ammonia. The precipitate formed is filtered off and rinsed with alcohol. The alcohol phase is concentrated and taken up with dichloromethane.

After this organic phase is washed with water, dried and concentrated, an orange oil is obtained which is taken up with cyclohexane. A solid is obtained.

M.p. 48.5°–50.5° C.

1.2. Ethyl 1-benzyl-4-chloro-2,3-dihydro-1H-indole-2-carboxylate.

In a 500-ml flask, there are introduced, under argon, 7.9 g (0.035 mole) of the ester obtained under 1., 7.7 g (0.056 mole) of $K_2CO_3$ and 100 ml of dimethylformamide, followed by 7.2 g (0.042 mole) of benzyl bromide.

The reaction mixture is stirred at room temperature for 24 h. It is poured into a mixture of water and ice and extracted with ether, and the extract is washed with water, dried and concentrated. An oil is obtained which is purified by chromatography on silica using cyclohexane/ethyl acetate (99:1) as eluant and which is used as it is in the following stage.

1.3. 2-(4,5-Dihydro-1H-imidazol-2-yl)-1-benzyl-4-chloro-2,3-dihydro-1H-indole and its fumarate.

To a solution of 2.9 g (0.0403 mole) of trimethylaluminium (16.5 ml of a 25% strength solution in hexane) in 30 ml of toluene, cooled to 0° C., a solution of 2.46 g (0.0410 mole) of ethylenediamine in 15 ml of toluene is added dropwise under argon in the course of 30 min.

This reaction mixture is brought to 50° C. and 5.3 g (0.0168 mole) of the ester obtained under 2., dissolved in 30 ml of toluene, are then added. The mixture is heated to 90° C., the hexane distilled off and the mixture brought to refluxing temperature for 4 h. The mixture is hydrolysed by adding water and cooled. The solution is filtered, rinsed with $CH_2Cl_2$ and extracted with $CH_2Cl_2$, and the extract is washed with water, dried and concentrated. A white solid is obtained. The compound obtained is converted to the fumarate by reacting 4.6 g (0.0148 mole) of the base dissolved in 50 ml of ethanol and 1.63 g (0.0140 mole) of fumaric acid dissolved in 100 ml of ethanol.

A white solid forms which, after filtration and recrystallization in methanol, melts at 229°–231° C.

EXAMPLE 2

2-(4,5-Dihydro-1H-imidazol-2-yl)-4-methyl-1-phenyl-2,3-dihydro-1H-indole and its fumarate.

2.1. 4-Methyl-1-phenyl-1H-indole-2-carboxamide.

To a solution of 10.9 g (0.0434 mole) of 4-methyl-1-phenyl-2-indolecarboxylic acid in 500 ml of $CH_2Cl_2$, 10.95 g (0.0675 mole) of carbonyldiimidazole are added portionwise.

The reaction mixture is stirred for 3 h at room temperature. It is then cooled in a mixture of water and ice and a stream of ammonia passed through. After ammonia has been bubbled through for 1 h, the reaction mixture is stirred at room temperature for 22 h. It is taken up in water and the precipitate removed. The organic phase is washed, dried and concentrated. A solid is obtained which is recrystallized in a toluene/ethyl acetate (1:1) mixture.

M.p. 187°–189° C.

2.2. 4-Methyl-1-phenyl-2,3-dihydro-1H-indole-2-carboxamide.

To a mixture of 100 ml of tetrahydrofuran and 200 ml of liquid ammonia, 8.6 g (0.0344 mole) of the amide obtained under 1. are added, and 1.74 g (0.5757 g-at) of sodium are then introduced in the course of 15 min. The reaction mixture is stirred for 30 min. It is hydrolysed with 100 ml of $NH_4Cl$ solution, and extracted with ethyl acetate, and the extract is washed with water, dried and concentrated.

After recrystallization in a toluene/ethyl acetate (1:2) mixture, a white solid is obtained.

M.p. 187°–189° C.

2.3. 4-Methyl-1-phenyl-2,3-dihydro-1H-indole-2-carbonitrile.

In a 250-ml three-necked flask, 7.0 g (0.0277 mole) of the amide obtained under 2. and 9.9 g (0.125 mole) of pyridine are introduced. 10.6 g (0.0555 mole) of p-toluenesulphonyl chloride are added slowly. The reaction mixture is stirred for 23 h at room temperature. It is poured into a mixture of water and ice and extracted with ether, and the extract is washed with 5% w/w aqueous hydrochloric acid, then with water, dried and concentrated in the cold. The oil obtained is taken up with cyclohexane. A white solid crystallizes.

M.p 98.5°–100.5° C.

2.4. 2-(4,5-Dihydro-1H-imidazol-2-yl)-4-methyl-1-phenyl-2,3-dihydro-1H-indole and its fumarate.

To a solution of 4.06 g (0.0563 mole) of trimethylaluminium (23.0 ml of a 25% strength solution in hexane) in 50 ml of toluene, a solution of 3.4 g (0.0569 mole) of ethylenediamine in 20 ml of toluene is added dropwise, under argon, at 0°–5° C. in the course of 30 min.

The reaction mixture is brought to 50° C. and 5.5 g (0.0235 mole) of the nitrile obtained under 3., dissolved in 50 ml of toluene, are added.

When the addition is complete, the mixture is heated to 90° C., the hexane distilled off and the mixture brought to refluxing temperature for 10 h. The mixture is hydrolysed while it is cooled with 60 ml of water. The solution obtained is filtered and rinsed with $CH_2Cl_2$. The organic phase is decanted, washed with water, dried and concentrated.

A white solid is obtained.

The fumarate is prepared by reacting 3.55 g (0.0128 mole) of base dissolved in 100 ml of ethanol with 1.4 g (0.0122 mole) of fumaric acid dissolved in 100 ml of ethanol.

An oil is obtained which is ground in acetone. The solid is recrystallized in isopropyl alcohol.

M.p. 199°–200.5° C.

EXAMPLE 3

2-(4,5-Dihydro-1H-imidazol-2-yl)-1-phenyl-2,3-dihydro-1Hindole.

3.1. 1-Phenyl-1H-indole-2-carboxamide.

To a suspension of 5.35 g (0.10 mole) of ammonium chloride in 100 ml of dry benzene at 5° C., 41.5 ml of a 25% strength solution of trimethylaluminium in hexane are added slowly. The dropping funnel is rinsed with 10 ml of dry benzene. The reaction mixture is allowed to return to room temperature and then stirred for 2 h.

To a solution of 8.0 g (0.03 mole) of ethyl 1-phenyl-1H-indole-2-carboxylate in 300 ml of benzene, 135 ml (0.09 mole) of the reagent prepared above are added. The reaction mixture is heated to 50° C. under argon for 12 h. It is hydrolysed with 50 ml of 5% strength HCl, filtered and washed with ethyl acetate. The organic phases are washed with water, dried and concentrated. A solid is obtained which is washed with toluene and recrystallized in acetone.

M.p. 193°–194.5° C.

3.2. 1-Phenyl-2,3-dihydro-1H-indole-2-carboxamide.

To a mixture of 175 ml of dry THF and 175 ml of liquid ammonia, 9.4 g (0.0398 mole) of 1-phenyl-1H-indole-2-carboxamide are added, and 2.0 g (0.088 gram-atom) of sodium are added in the course of 10 min and the mixture is then stirred for 30 min. It is hydrolysed with 100 ml of NH$_4$Cl solution, and extracted with ethyl acetate, and the extract is washed with water, dried and concentrated. The solid obtained is recrystallized in toluene.

M.p. 190°–191.5° C.

3.3. 1-Phenyl-2,3-dihydro-1H-indole-2-carbonitrile.

In a 250-ml three-necked flask, 6.0 g (0.025 mole) of 1-phenyl-2,3-dihydro-1H-indole-2-carboxamide and 9.0 g (9.2 ml; 0.113 mole) of pyridine are introduced. 9.5 g (0.050 mole) p-toluenesulphonyl chloride are added slowly and the reaction mixture is stirred for 3 h 30 min at room temperature. The reaction mixture is poured into water and ice and extracted with ether, and the extract is washed with 5% strength hydrochloric acid, then with water, dried and concentrated in the cold. The oil formed is taken up in cyclohexane. The cyclohexane phase is concentrated and a solid is obtained.

M.p. 47.5°–49° C.

3.4. 2-(4,5-Dihydro-1H-imidazol-2-yl)-1-phenyl-2,3-dihydro-1H-indole.

A solution of 2.2 g (0.01 mole) of 1-phenyl-2,3-dihydro-1H-indole-carbonitrile in 1.8 g (2.06 ml; 0.03 mole) of ethylenediamine is saturated with H$_2$S at 0° C. The mixture is left to stand at room temperature for 4 days. The solid formed is taken up with CH$_2$Cl$_2$ and the organic phase washed 3 times with water, dried and concentrated. An oil is obtained.

The fumarate of the compound obtained is prepared by reacting 3.5 g (0.0133 mole) of base dissolved in 50 ml of ethanol and 1.4 g (0.0120 mole) of fumaric acid dissolved in 80 ml of ethanol. The solution is concentrated and the concentrate taken up with ethyl acetate and ground. A solid is obtained which is recrystallized in ethanol.

M.p. 212.5°–215° C.

The table below illustrates the structures and physical properties of a few compounds according to the invention.

TABLE

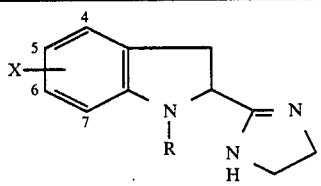

| Compound | X | R | Salt or base (*) | M.p. (°C.) |
|---|---|---|---|---|
| 1 | 4-Cl | benzyl | 08 | 229–231 |
| 2 | 4-Cl | allyl | 08 | 200–201.5 |
| 3 | 4-Cl | n-propyl | 08 | 179.5–181 |
| 4 | 4-Cl | cyclopropylmethyl | 08 | 202–203.5 |
| 5 | 4-MeO | benzyl | 08 | 198–199 |
| 6 | 6-F | benzyl | 08 | 174–176 |
| 7 | 6-Me | benzyl | 08 | 159–161 |
| 8 | 6-Me | allyl | 08 | 184–185 |
| 9 | 6-Me | cyclopropylmethyl | 08 | 178–180 |
| 10 | 4-allyloxy | benzyl | 00 | 154–155 |
| 11 | 4-allyloxy | n-butyl | 08 | 115–117 |
| 12 | 4-allyloxy | n-pentyl | 00 | 102–103 |
| 13 | 5-MeO | benzyl | 08 | 152–154.5 |
| 14 | 5-MeO | ethyl | 00 | 130–132 |
| 15 | 5-MeO | isobutyl | 00 | 153–154.5 |
| 16 | 6-allyloxy | benzyl | 10 | 149–152 |
| 17 | 6-n-propyloxy | benzyl | 10 | 161–164 |
| 18 | 4-Me | benzyl | 10 | 201–204 |
| 19 | 4-Me | allyl | 10 | 187–189 |
| 20 | 7-Cl | allyl | 10 | 219–221 |
| 21 | 7-Cl | benzyl | 10 | 209–211 |
| 22 | 7-F | allyl | 10 | 175–177 |
| 23 | 7-F | benzyl | 10 | 104–108 |
| 24 | 7-F | cyclopropylmethyl | 10 | 212–214 |
| 25 | 4-F | allyl | 10 | 189–192 |
| 26 | 4-F | benzyl | 10 | 187–189 |
| 27 | 4-F | cyclopropylmethyl | 10 | 169–171 |
| 28 | 4-F | n-propyl | 10 | 170–172 |
| 29 | 4-F | n-pentyl | 10 | 173–175 |
| 30 | 4-F | n-hexyl | 10 | 164–166 |
| 31 | 4-Cl | 2-Cl—benzyl | 10 | 184 |
| 32 | 4-Cl | 2-MeO—benzyl | 10 | 204–206 |
| 33 | 4-Cl | 2-F—benzyl | 10 | 192–193 |
| 34 | 4-Cl | 4-Me—benzyl | 10 | 258–262 |
| 35 | 4-Cl | 2-Me—benzyl | 10 | 214–218 |
| 36 | H | phenyl | 08 | 212.5–215 |
| 37 | H | 4-Me—phenyl | 08 | 199–201 |
| 38 | H | 3-MeO—phenyl | 08 | 157–160 |
| 39 | H | 4-MeO—phenyl | 08 | 89–93(**) |
| 40 | H | 3-Me—phenyl | 08 | 174–175 |
| 41 | 4-Me | phenyl | 08 | 199–200.5 |
| 42 | 4-Me | 4-MeO—phenyl | 00 | 169.5–171.5 |
| 43 | H | 4-Et—phenyl | 08 | 127–130 |
| 44 | H | 4-EtO—phenyl | 08 | 124–127 |
| 45 | H | 3-EtO—phenyl | 08 | 151–153 |
| 46 | H | 3-PrO—phenyl | 08 | 157–159 |
| 47 | H | 3-Et—phenyl | 08 | 158–161.5 |
| 48 | H | 3-Pr—phenyl | 08 | 135–137 |
| 49 | 5-MeO | phenyl | 08 | 194–196 |

(*) 00: base
08: fumarate
10: hydrochloride
(**) hemihydrate

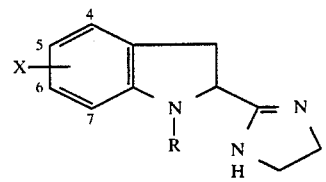

The compounds of the invention were subjected to pharmacological experiments which showed their value as α$_2$-antagonists.

To this end, the compounds were studied in the tests of potentiality and selectivity of the antagonists in respect of α$_2$ receptors in vitro.

The determination of the pA$_2$ value in respect of the inhibitory effects of clonidine, a well-known α$_2$-agonist, was carried out on rat vas deferens stimulated at a frequency of 0.1 Hz in the presence of 300 nM prazosin and 1 μM cocaine, according to the method described by G. M. Drew [European Journal of Pharmacology, 42, (1977) 123–130].

The pA$_2$ values of the compounds of the invention are between 6 and 11.

Some of the compounds are substances which cause powerful contractions in vitro of a rabbit pulmonary artery preparation (preparation containing, at the post-synaptic level, only α$_1$ receptors), according to Starke et al 1975, Naunyn Schmiedeberg's Arch. Pharamacol., 291, 55–78.

The concentration of compound (I) required for obtaining 50% of the maximum contraction (EC$_{50}$) ranges from 10 μM to 0.1 μM.

These compounds are indeed α$_1$-receptor agonists, since the contractions which they induce in the rabbit pulmonary artery preparation are antagonized by prazosin, an α$_1$-receptor antagonist.

They can hence be used in therapy, for example as nasal vasoconstrictors.

We claim:

1. A compound of formula (I)

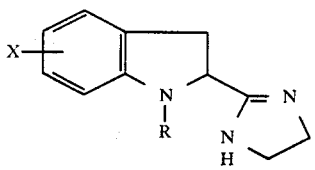

(I)

in which
X is halogen (C$_{1-4}$)alkoxy, (C$_{1-4}$)alkyl or allyloxy or, when R is substituted or unsubstituted phenyl, X can also denote a hydrogen atom and
R is linear or branched (C$_{1-6}$)alkyl, (C$_{3-6}$)cycloalkyl-(C$_{1-4}$)alkyl, (C$_{3-6}$)alkenyl, benzyl which is unsubstituted or substituted by one or more halogen, methyl, methoxy and methylenedioxy substituents, or phenyl of formula

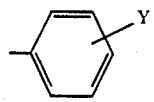

in which Y is hydrogen, halogen, linear or branched (C$_{1-6}$)alkyl or linear or branched (C$_{1-6}$)alkoxy or an addition salt thereof with a pharmaceutically acceptable acid.

2. A racemic compound of formula (I) according to claim 1.

3. An optically active isomer of formula (I) according to claim 1.

4. A compound according to claim 1, wherein X is chlorine, fluorine, methyl, methoxy or allyloxy and R is alkyl, benzyl, allyl or cyclopropylmethyl.

5. A compound according to claim 1, wherein X is at position 4, 6 or 7.

6. A compound according to claim 1, wherein X is hydrogen or methyl and R is phenyl, methylphenyl, ethylphenyl, propylphenyl, methoxyphenyl, ethoxyphenyl or propoxyphenyl radical.

7. A compound according to claim 6, wherein X is at position 4 and R Is a phenyl group substituted at position 3 or 4.

8. A pharmaceutical composition for use as an α$_2$ receptor antagonist comprising an effective antagonist amount of a compound of claim 1 and a suitable excipient.

9. A composition according to claim 8, presented for oral, rectal or parenteral administration.

10. A pharmaceutical composition for use as an α$_1$-receptor agonist comprising an effective agonist amount of a compound of claim 1 having α$_1$ receptor agonist activity and a suitable excipient.

11. A composition according to claim 10, presented for external or local administration.

12. A method for treating the human or animal body comprising administering an effective α$_2$-receptor antagonist or α$_1$-receptor agonist amount of a compound of formula (I) as defined in claim 1, to a human or animal in need thereof.

13. A method according to claim 12, for treating depression, hypotension, postoperative paralytic ileum, asthma, obesity, diabetes or impotence.

14. A method according to claim 12, for effecting nasal vasoconstriction or for treating nasal congestion comprising administering externally or locally a compound of formula (I) having α$_1$ receptor agonist activity.

15. A method according to claim 12, comprising administering of compound of formula (I) in an amount of from 0.1 to 10 mg per kg of body weight.

* * * * *

Notice of Adverse Decision in Interference

In Interference No. 101,836, involving Patent No. 4,659,731, D. Bigg and J. Menin, 2-(4,5-DIHYDRO-1H-IMIDAZOL-2-YL)-2, 3-DIHYDROINDOLE DERIVATIVES AND THEIR APPLICATION AS $a_2$ RECEPTOR ANTAGONIST OR $a_1$ RECEPTOR AGONISTS, final judgment adverse to the patentees was rendered March 3, 1989, as to claims 1-9, 12, 13 and 15.

[*Official Gazette November 21, 1989*]